(12) United States Patent
Hoyt

(10) Patent No.: US 11,725,181 B2
(45) Date of Patent: *Aug. 15, 2023

(54) BIOGAS BUFFER STORAGE SYSTEM

(71) Applicant: Trillium Transportation Fuels, LLC, Houston, TX (US)

(72) Inventor: Carson Hoyt, Houston, TX (US)

(73) Assignee: Trillium Transportation Fuels, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/970,228

(22) Filed: Oct. 20, 2022

(65) Prior Publication Data
US 2023/0062071 A1    Mar. 2, 2023

Related U.S. Application Data

(63) Continuation of application No. 16/861,480, filed on Apr. 29, 2020, now Pat. No. 11,479,750.

(60) Provisional application No. 62/841,968, filed on May 2, 2019.

(51) Int. Cl.
*C12M 1/00*     (2006.01)
*B01D 53/26*    (2006.01)
*B01D 53/52*    (2006.01)
*C10L 3/08*     (2006.01)

(52) U.S. Cl.
CPC .......... *C12M 47/18* (2013.01); *B01D 53/265* (2013.01); *B01D 53/52* (2013.01); *C10L 3/08* (2013.01); *C12M 47/10* (2013.01); *B01D 2257/304* (2013.01); *B01D 2257/80* (2013.01); *B01D 2258/05* (2013.01)

(58) Field of Classification Search
CPC .. B01D 2258/05; B01D 63/265; B01D 53/52; B01D 2257/60; C10L 31/08; C12M 47/18
See application file for complete search history.

(56) References Cited

U.S. PATENT DOCUMENTS

2015/0101671 A1    4/2015  Paget et al.

*Primary Examiner* — Jafar F Parsa
(74) *Attorney, Agent, or Firm* — Banner & Witcott, Ltd.

(57) ABSTRACT

Processes, systems, and associated control methodologies are disclosed that control the flow of biogas during the biogas cleanup process to create a more consistent flow of biogas through the digester, while also optimizing the output and efficiency of the overall renewable natural gas facility. In representative embodiments, a biogas buffer storage system may be used during the cleanup process to control the pressure and flow rate of biogas. The biogas buffer storage system may monitor and control the biogas flow rate to either bring down or increase the digester pressure, thereby maintaining a normalized biogas flow rate.

20 Claims, 1 Drawing Sheet

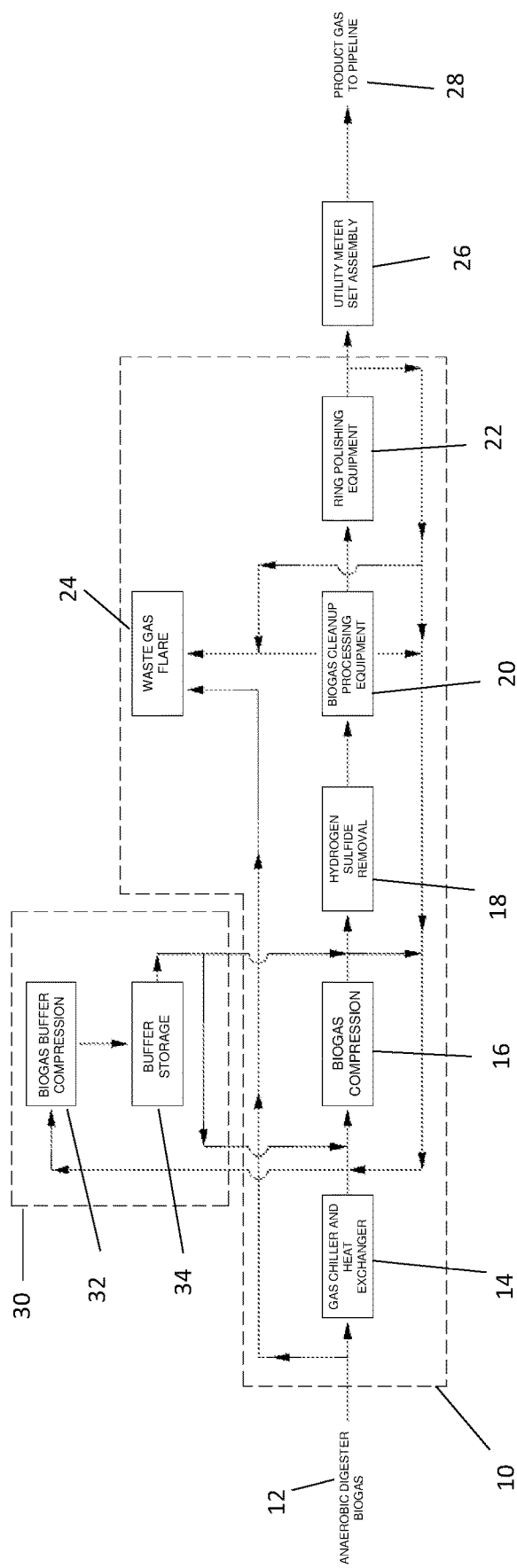

BIOGAS BUFFER STORAGE SYSTEM

CROSS-REFERENCE TO RELATED APPLICATION

This application is continuation of U.S. application Ser. No. 16/861,480, filed Apr. 29, 2020, which is a non-provisional application of and claims benefit to U.S. Provisional Application No. 62/841,968, filed May 2, 2019, which is incorporated herein by reference in its entirety.

FIELD

The exemplary embodiments relate generally to methods and systems for controlling the pressure and/or flow rate of biogas during the biogas cleanup process at a renewable natural gas facility.

BACKGROUND

It is known that existing renewal natural gas facilities receive biogas from waste water treatment plants and sometimes from dairies. Many of these biogas facilities utilize anaerobic digesters to extract the biogas from the bio-solids, which are captured in the water treatment process at waste water facilities or from manure captured at dairies. This same process is also used for anaerobic digesters used with food waste and other organic manufacturing waste.

A drawback with the anaerobic digester process is sometimes there is not always a continuous flow of biogas through and from the digester. This is due to many factors, including the quality of the input material, whether the flow of the input material is consistent, and the temperature inside and outside the digester, among other factors. It is desirable that the pressure inside the digester be maintained at a constant pressure to continue the biogas cleanup process. If the pressure inside the digester gets too high, the system and structure may be damaged.

It is also known that the pressure inside the digester can fluctuate significantly. When the pressure increases suddenly, a flare is started which bypasses the renewable natural gas facility and the excess biogas is burned. Due to the sizing of some flares, this also takes additional gas from the renewable natural gas facility resulting in a shutdown of the plant due to lack of biogas. This shutdown results in lost revenue and additional costs to safely restart the system after a shutdown. These fluctuations in pressure from the digester also cause operation issues in the renewable natural gas facility.

The embodiments described herein are directed toward overcoming the described problems, including the problems associated with digester biogas pressure/output fluctuations.

SUMMARY OF THE INVENTION

Aspects of the invention relate to processes, systems, and associated control methodologies to control the pressure and/or flow rate of biogas during the biogas cleanup process in a renewable natural gas facility to ensure the biogas flow is more consistent during the biogas cleanup process. These processes, systems, and control methodologies also optimize the output and efficiency of the overall renewable natural gas facility.

In a representative embodiment of the invention, for example, a biogas buffer storage system may be used that controls the pressure and flow rate of biogas in the digester during the biogas cleanup process. In representative embodiments, a control system may be used to monitor the biogas pressure in the digester or at an outlet line. This may be achieved through the use of a pressure transmitter connected to a buffer storage system controller. Once a pressure increase is detected in the digester or the outlet line, the buffer storage system controller will start a buffer screw compressor or similar compressor. The screw compressor may be controlled by a control system and may have variable frequency drive capability to modulate the speed and flow rate of the biogas.

In an exemplary aspect, the buffer screw compressor output will be modulated to draw down the excess pressure from the digester without reducing the digester pressure below normal operating conditions. This will equalize the pressure in the digester back to normal operating conditions. In another exemplary aspect, once normal operating conditions are achieved in the digester, the buffer screw compressor may be returned to a standby state. By providing means to modulate the digester pressure the excess biogas is captured and no longer wasted to a destructive flare.

In further representative embodiments, the biogas compressed by the buffer screw compressor may be stored in a buffer storage vessel. The buffer storage vessel may be designed with sufficient capacity to allow for capture of biogas from multiple digester pressure buildups. In yet a further representative embodiment, the biogas stored in the buffer storage vessel may be regulated back to the biogas cleanup stream when biogas flow from the digester is low.

With the representative embodiments disclosed herein, the buffer storage system of the invention provides the advantage of keeping the biogas stream more consistent by bringing the biogas flow to a normal flow rate, while also optimizing the output and efficiency of the overall system. Having a normal flow rate also has the advantage of providing more efficiently the increased quality of the biogas output stream.

BRIEF DESCRIPTION OF THE DRAWINGS

A more complete understanding of the exemplary embodiments of the present invention and the advantages thereof may be acquired by referring to the following description in consideration of the accompanying figures, in which the same reference numbers are used to designate the same or similar features, and wherein:

FIG. 1 depicts an embodiment of a process and associated system, which can be used to control the pressure and/or flow rate of biogas during the biogas cleanup process in a renewable natural gas facility to ensure the biogas flow is more consistent during the biogas cleanup process, as described herein.

FIG. 1 should be understood to present an illustration of the invention and principles involved. Simplified systems and process flows are depicted, and some components may be distorted/enlarged relative to others, in order to facilitate explanation and understanding. Optional equipment and other items not essential to the understanding of the invention, which may include some instrumentation, some process lines, heaters and coolers, etc., are not shown. As is readily apparent to one of skill in the art having knowledge of the present disclosure, processes and associated equipment for controlling the pressure and/or flow rate of the biogas, according to various other embodiments of the invention, will have configurations and components determined, in part, by their specific use.

DESCRIPTION OF THE EMBODIMENTS

Exemplary embodiments of the application relate to methods and systems for controlling the pressure and/or flow rate of biogas during the biogas cleanup process in a renewable natural gas facility to ensure the biogas flow is more consistent during the biogas cleanup process. The exemplary embodiments also optimize the output and efficiency of the overall biogas cleanup system. As described herein, exemplary aspects relate to processes, systems, and associated control methodologies that control the flow of biogas to create a steady flow of biogas through the digester, while simultaneously improving the efficiency of the overall cleanup process in the renewable natural gas facility.

The processes, systems and associated control methodologies described herein have multiple benefits to both the operation of the digester and the renewable natural gas facility. These benefits include, without limitation: 1) helping the digester operate more efficiently by controlling the pressure inside the digester rather than reacting to it; 2) reducing the amount of biogas that is lost due to operation of the flare; 3) increasing the amount of biogas that can be processed by the renewable natural gas plant; and 4) providing laminar or steady biogas flow thereby increasing the efficiency of the renewable natural gas plant's operation and production.

Referring to FIG. 1, there is shown an exemplary aspect of the invention and includes a biogas flow path 10 of a biogas cleanup process along with a buffer compression and storage system 30 of the invention that is integrated with the flow path 10 to create a more consistent flow of biogas through the digester.

As depicted in FIG. 1, the biogas flow path 10 may include the supply of anaerobic digester biogas 12 to a gas chiller and heat exchanger 14. The first step in biogas cleanup is to provide initial cleanup of water and hydrogen sulfide. The gas chiller and heat exchanger 14 lowers the temperature of the gas which also lowers the dew point at the same pressure. This allows water in the gas stream to condensate and form liquid water. This water can then be collected and removed from the gas stream. After the water is removed, the gas is run through a heat exchanger to bring the temperature back to near ambient temperature.

After the biogas is back to near ambient temperature, the biogas is then compressed at step 16 by one or more biogas compressors. During this step, one or more compressors are used to increase the pressure of the biogas. A higher pressure is needed for proper operation of the subsequent steps in the biogas cleanup process. In one embodiment, the one or more compressors can be operating at a vacuum in some facilities to "suck" the gas out of the digesters and piping systems.

The next step in the biogas cleanup process is the removal of hydrogen sulfide. At step 18, a large vessel filled with activated carbon or other media, such as iron sponges and biologic media, is used to remove hydrogen sulfide from the biogas. As the biogas flows through the carbon or other media, the hydrogen sulfide is absorbed resulting in significantly diminished hydrogen sulfide levels at the outlet of the vessel. The carbon or other media is non-regeneratable and will need to be replaced once saturated.

After the hydrogen sulfide is removed, at step 20, the biogas is delivered to biogas cleanup processing equipment. At this step, there are two different types of equipment that may be used depending on what contaminates need to be removed from the biogas. In some instances, both of the following equipment and processes may be used together to remove the waste gases. One type of equipment is a membrane. With the membrane, biogas is directed into small tubes that allow one type of molecule to flow through while another passes through the tube wall. The methane is harvested and is allowed to flow downstream while the waste gas is collected and sent to the flare or thermal oxidizer 24. The flare or thermal oxidizer 24 is used to safely and efficiently destroy the waste gases generated during the biogas cleanup process. The other type of equipment is a pressure swing absorber. With the pressure swing absorber, as biogas flows through a media, such as zeolites, activated carbon, and molecular sieves, some molecules are collected while others pass through. Once saturated, the vessel is depressurized releasing the trapped molecules. The methane is harvested and is allowed to flow downstream while the waste gas is collected and sent to the flare or thermal oxidizer 24.

The next step in the biogas cleanup process is at step 22 where the gas is cleaned to meet certain quality specifications. At step 22, one or more vessels containing activated carbon are used and are designed to absorb residual contaminates from the biogas stream and to "polish" the gas to meet utility gas quality specifications before the gas is delivered to the external utility network.

Once polished, at step 26, the biogas is sent through a utility meter set assembly. This assembly contains gas quality monitoring and measuring equipment to verify the quality of the biogas before the biogas is allowed to enter the external utility network.

As indicated above, a known problem with the biogas cleanup process is there is not always a continuous flow of biogas from the digester. This is due to many factors, as described above. The pressure inside the digester needs to be maintained to continue the process, it cannot get too high or the structure could be damaged. It is also known that the pressure inside the digester can fluctuate significantly. To overcome these problems, a buffer compression and storage system 30 may be incorporated into the biogas cleanup process.

In an exemplary aspect, the buffer compression and storage system 30 will monitor the biogas pressure in the digester or at an outlet line, whichever is available, utilizing a 4-20 mA pressure transmitter connected to the buffer storage system controller. Once a pressure increase is detected in the digester or outlet line, the buffer storage system controller will start one or more buffer screw compressors, at step 32. The screw compressor will be powered by an electric motor of varying kilowatt ratings depending on the requirements and flow rates of the system. Other types of compressors can be used at this step. In an exemplary aspect, the biogas pressure in the digester may be detected at the outlet line of the gas chiller and heat exchanger 14 prior to the biogas passing to the biogas compressor 16.

The screw compressor at step 32 may be controlled by a control system and may have variable frequency drive capability to modulate the speed and flow rate. The buffer screw compressor output will be modulated to draw down or lower the excess pressure from the digester without reducing the digester pressure below normal operating conditions. This will create a regulated supply of biogas from the digester. This will also provide the benefit of equalizing the pressure in the digester back to normal operating conditions. By providing means to modulate the digester pressure the excess gas is captured and no longer wasted to a destructive flare, or requiring ramp up of the overall production facility. Once normal operating conditions are achieved in the digester, the buffer screw compressor will be returned to a standby state.

It should be understood that the regulated biogas supply may be transferred back to the biogas flow path of the digester at one or more different stages of the cleanup process, including prior to the removal of the hydrogen sulfate at step 18, or prior to the biogas compression at step 16, as depicted by FIG. 1. In an alternative aspect, the regulated biogas supply may be transferred back to the biogas flow path of the digester at other stages, including after the hydrogen sulfate is removed at step 18, or before or after the methane is separated from the waste gas at step 20, or before or after the residual contaminants are removed at step 22. As should be understood, the biogas compression and storage system 30 may be implemented into the biogas cleanup process at any of the many stages of the cleanup process.

The biogas compressed by the buffer screw compressor will be stored in a buffer storage vessel or container, at step 34. The buffer storage vessel or container will be designed with adequate capacity to allow for capture of gas from multiple digester pressure buildups. The biogas in the buffer storage vessel will be regulated to the biogas flow path, between the biogas compression step 16 and the hydrogen sulfide removal step 18, when biogas flow from the digester is low. The biogas in the buffer storage vessel may also be regulated to the biogas flow path at other stages of the biogas cleanup process, as explained above. This system will also allow for consistent production increase as the pressure can be let out of storage over a longer period of time to simply increase the cleanup facility output. These scenarios provide the advantage of keeping the biogas stream more consistent by bringing the biogas flow to a normal flow rate, while also optimizing the output and efficiency of the overall system. Normalizing the flow rate also has the advantage of providing increased quality of the output stream more efficiently.

In an exemplary embodiment, the biogas output stream from the buffer storage vessel or container 34 will be metered and controlled utilizing a control system that further controls one or more control valves. The control system will also incorporate multiple pressure transmitters to accurately measure the pressure in the system. One or more control valves may be used to control the biogas flow rate in the system. The control valves will be controlled via a proportional-integral-derivative (PID) loop to keep pressures consistent therefore normalizing flow rates throughout the system.

In an exemplary process for controlling the flow of biogas during the biogas cleanup process in a renewable natural gas facility, one more aspects of the invention may include supplying biogas to a chiller and heat exchanger of a biogas digester, wherein the chiller and heat exchanger lowers the temperature of the biogas to allow water in the biogas stream to condensate and form liquid water, wherein the water is removed from the bio gas stream, and wherein the biogas passes through a heat exchanger to raise the temperature of the biogas.

Additional aspects may include detecting the biogas pressure at an outlet line from the chiller and heat exchanger, and supplying the biogas to a buffer compressor, wherein the buffer compressor is controlled by a control system to either lower the biogas pressure or increase the biogas pressure to create a regulated supply of biogas. Further aspects may include storing any excess biogas buildup in a buffer storage vessel or container, transferring the regulated biogas supply back to the biogas cleanup process, removing any hydrogen sulfide from the regulated biogas, removing any methane from the regulated biogas, and supplying the regulated biogas to an external utility network.

Additional features of the buffer compressor may include controlling the compressor by a control system that further includes multiple pressure transmitters to accurately measure the biogas pressure, and that further includes variable frequency drive capability to modulate the speed and flow rate of the biogas. In an exemplary aspect, the buffer compressor may be one or more screw compressors that will lower or raise the biogas pressure without reducing the digester pressure below operating conditions.

Yet additional aspects may include transferring the excess biogas buildup in the buffer storage container back to the biogas cleanup process. Further aspects may include absorbing residual contaminates from the regulated biogas after the methane has been removed from the biogas, wherein one or more vessels containing carbon may be used to absorb the residual contaminates. In additional aspects, the methane may be separated from waste gas through the use of a membrane, and wherein the waste gas is transferred to a flare or thermal oxidizer to be burned up. The regulated biogas may also be transferred to quality monitoring and measuring equipment to verify the quality of the biogas before the biogas is allowed to enter the external utility network.

In another exemplary process for controlling the flow of biogas during the biogas cleanup process in a renewable natural gas facility, one more aspects of the invention may include supplying biogas to a chiller and heat exchanger of a biogas digester, detecting the biogas pressure at an outlet line from the chiller and heat exchanger, and supplying the biogas to a buffer compressor and storage system. The buffer compressor and storage system may include a buffer screw compressor that is controlled by a control system to either lower the biogas pressure or increase the biogas pressure to create a regulated supply of biogas, and a buffer storage container for storing biogas. The control system may further include at least one pressure transmitter to measure the biogas pressure. Additional aspects of the process may include transferring the regulated biogas supply back to the biogas cleanup process, storing any excess biogas in the buffer storage container, removing hydrogen sulfide from the regulated biogas, removing methane from the regulated biogas, absorbing residual contaminates from the regulated biogas after the methane has been removed from the biogas, and supplying the regulated biogas to an external utility network.

In an aspect of the process, the buffer compressor may be controlled by multiple pressure transmitters to accurately measure the biogas pressure, and may be controlled by a control system that has variable frequency drive capability to modulate the speed and flow rate of the biogas. Further aspects include a buffer compressor that will lower or raise the biogas pressure without reducing the digester pressure below operating conditions.

In yet another aspect of the process, the excess biogas from the buffer storage container may be transferred back to the biogas cleanup process, and one or more vessels containing carbon may be used to absorb the residual contaminates. Additionally, the methane may be separated from waste gas through the use of a membrane, wherein the waste gas is transferred to a flare or thermal oxidizer to be burned up.

Further, the regulated biogas may be transferred to quality monitoring and measuring equipment to verify the quality of the biogas before the biogas is allowed to enter the external utility network. Also, one or more control valves may be used to control the biogas flow rate throughout the system, wherein the control valves may be controlled through the use of a proportional-integral-derivative loop to keep the biogas pressure consistent.

Those having skill in the art, with the knowledge gained from the present disclosure, will recognize that various changes could be made in these processes and systems, without departing from the scope of the present invention. While in the foregoing specification the invention has been described in relation to certain preferred embodiments thereof, and details have been set forth for purpose of illustration, it will be apparent to those skilled in the art that the disclosure is susceptible to additional embodiments, based on modification, alteration, changes or substitution of various features described herein, without departing significantly from the spirit of the disclosure. For example, the dimensions, number, size and shape of the various components may be altered to fit specific applications. Accordingly, the specific embodiments illustrated and described herein are for illustrative purposes only, and not limiting of the invention.

What is claimed is:

1. A process for controlling the flow of biogas during the biogas cleanup process in a renewable natural gas facility, the process comprising:
    supplying biogas to a chiller and heat exchanger of a biogas digester, wherein the chiller and heat exchanger lowers the temperature of the biogas to allow water in the biogas stream to condensate and form liquid water, wherein the water is removed from the biogas stream, and wherein the biogas passes through a heat exchanger to raise the temperature of the biogas;
    detecting the biogas pressure at an outlet line from the chiller and heat exchanger;
    supplying the biogas to a buffer compressor, wherein the buffer compressor is controlled by a control system to either lower the biogas pressure or increase the biogas pressure to create a regulated supply of biogas;
    storing any excess biogas buildup in a buffer storage container;
    transferring the regulated biogas supply back to the biogas cleanup process; and
    supplying the regulated biogas to an external utility network.

2. The process of claim 1, wherein the buffer compressor is controlled by a control system that further includes multiple pressure transmitters to accurately measure the biogas pressure.

3. The process of claim 1, wherein the buffer compressor is controlled by a control system that has variable frequency drive capability to modulate the speed and flow rate of the biogas.

4. The process of claim 2, wherein the buffer compressor is a screw compressor that will lower or raise the biogas pressure without reducing the digester pressure below operating conditions.

5. The process of claim 2, further comprising transferring the excess biogas buildup in the buffer storage container back to the biogas cleanup process.

6. The process of claim 1, further comprising removing hydrogen sulfide and methane from the regulated biogas.

7. The process of claim 6, further comprising absorbing residual contaminates from the regulated biogas after the methane has been removed from the biogas.

8. The process of claim 6, wherein the methane is separated from waste gas through the use of a pressure swing absorber.

9. The process of claim 2, wherein one or more control valves are used to control the biogas flow rate, and wherein the control valves will be controlled through the use of a proportional-integral-derivative loop to keep the biogas pressure consistent.

10. The process of claim 1, wherein the regulated biogas is transferred to quality monitoring and measuring equipment to verify the quality of the biogas before the biogas is allowed to enter the external utility network.

11. A process for controlling the flow of biogas during the biogas cleanup process in a renewable natural gas facility, the process comprising:
    supplying biogas to a chiller and heat exchanger of a biogas digester;
    detecting the biogas pressure at an outlet line from the chiller and heat exchanger;
    supplying the biogas to a buffer compressor and storage system, wherein the buffer compressor and storage system includes a buffer screw compressor that is controlled by a control system to either lower the biogas pressure or increase the biogas pressure to create a regulated supply of biogas, and a buffer storage container for storing biogas, wherein the control system further includes at least one pressure transmitter to measure the biogas pressure;
    transferring the regulated biogas supply back to the biogas cleanup process;
    storing any excess biogas in the buffer storage container;
    removing methane from the regulated biogas;
    absorbing residual contaminates from the regulated biogas after the methane has been removed from the biogas; and
    supplying the regulated biogas to an external utility network.

12. The process of claim 11, wherein the buffer compressor is controlled by multiple pressure transmitters to accurately measure the biogas pressure.

13. The process of claim 12, wherein the buffer compressor is controlled by a control system that has variable frequency drive capability to modulate the speed and flow rate of the biogas.

14. The process of claim 11, wherein the buffer compressor will lower or raise the biogas pressure without reducing the digester pressure below operating conditions.

15. The process of claim 14, further comprising transferring the excess biogas from the buffer storage container back to the biogas cleanup process.

16. The process of claim 11, wherein one or more vessels containing carbon are used to absorb the residual contaminates.

17. The process of claim 11, wherein the methane is separated from waste gas through the use of a membrane and wherein the waste gas is transferred to a flare or thermal oxidizer.

18. The process of claim 17, further comprising removing hydrogen sulfide from the regulated biogas.

19. The process of claim 14, wherein the regulated biogas is transferred to quality monitoring and measuring equipment to verify the quality of the biogas before the biogas is allowed to enter the external utility network.

20. The process of claim 19, wherein one or more control valves are used to control the biogas flow rate, and wherein the control valves will be controlled through the use of a proportional-integral-derivative loop to keep the biogas pressure consistent.

* * * * *